United States Patent [19]

Hitze et al.

[11] Patent Number: 4,921,987
[45] Date of Patent: May 1, 1990

[54] AQUEOUS SOLUTIONS OF ALKYLTRIALKOXYSILANES HAVING AN EXTENDED SHELF LIFE

[75] Inventors: Reiner Hitze; Hans-Jürgen Hass, both of Troisdorf, Fed. Rep. of Germany

[73] Assignee: Huels Aktiengesellschaft, Troisdorf, Fed. Rep. of Germany

[21] Appl. No.: 395,345

[22] Filed: Aug. 17, 1989

[30] Foreign Application Priority Data

Aug. 31, 1988 [DE] Fed. Rep. of Germany ....... 3829510

[51] Int. Cl.$^5$ .............................. C07F 7/08; C07F 7/18
[52] U.S. Cl. ................................... 556/401
[58] Field of Search ........................................ 556/401

[56] References Cited

U.S. PATENT DOCUMENTS 3,948,964  4/1976  Barfurter et al. .................... 556/401
4,503,242  3/1985  Plueddermann ..................... 556/401

FOREIGN PATENT DOCUMENTS 0072197  5/1980  Japan .................................... 556/401

Primary Examiner—Paul F. Shaver
Attorney, Agent, or Firm—Felfe & Lynch

[57] ABSTRACT

Aqueous solutions of alkyltrialoxysilanes are stabilized by adding an alkali metal aluminate and an alkali metal hydroxide thereto.

5 Claims, No Drawings

AQUEOUS SOLUTIONS OF ALKYLTRIALKOXYSILANES HAVING AN EXTENDED SHELF LIFE

FIELD OF THE INVENTION

This invention relates to stable, non-combustible, aqueous solutions of alkyltrialkoxysilanes which contain an alkali metal aluminate and an alkali metal hydroxide as stabilizers.

BACKGROUND OF THE INVENTION AND THE PRIOR ART

West German Patent (DE-PS) No. 36 31 834 discloses that solutions of trialkoxysilanes are only very briefly stable in the presence of water, that is, for only a few hours. Depending on the concentration of the alkyltrialkoxysilane, the silicon compound precipitates within a few hours to several days in the form of insoluble, oily, polymeric siloxanols. It has therefore been proposed to stabilize such solutions by adding alkali metal silicates thereto. Such a stabilization, however, is not feasible when the silane concentrations are high.

When alkyltrialkoxysilanes are used in aqueous solution, therefore, the silicon compound must be transported as such to the point of use where it must be processed. Due to the long periods of time that are necessary for the preparation of clear, uniform solutions, for example, this entails processing problems. Furthermore, alkyltrialkoxysilanes with aliphatic moieties containing 1 to 4 carbon atoms are flammable liquids whose vapor can form explosive mixtures with air. The transportation and handling of these substances is thus made difficult, and costly safety measures are required.

OBJECTS OF THE INVENTION

It is an object of the present invention to provide nonflammable aqueous solutions of alkyltrialkoxysilanes having an acceptable shelf life and high, economically adequate silane concentrations.

Other objects and advantages of this invention will become apparent as the description thereof proceeds.

DESCRIPTION OF THE INVENTION

The aforesaid object is achieved in accordance with the present invention by an aqueous solution of alkyltrialkoxysilanes to which an alkali metal aluminate and an alkali metal hydroxide are added as stabilizers. We have discovered that the addition of these compounds makes aqueous solutions of alkyltrialkoxysilanes stable even at high silane concentrations. The solutions thus obtained can be stored for several days to several months without observing any appreciable changes. The solutions according to the present invention can be varied in their pH value or heated at the boiling point for several hours without affecting their stability.

A solution of the instant invention is prepared by first dissolving an alkyltrialkoxysilane or a mixture of two or more of these in water. This can be done, for example, by adding catalytically active amounts of organic or inorganic acids. This solution is then admixed with an aqueous solution of an alkali metal aluminate and an alkali metal hydroxide containing these substances in the desired amount. To prepare the solutions of the invention, however, it is also possible to add the alkali metal aluminate and the alkali metal hydroxide in separate solutions in the desired amount to the alkyltrialkoxysilane solution.

Examples of suitable alkali metal aluminate solutions are commercial sodium aluminate solutions with a molar ratio of $Na_2O:Al_2O_3$ of more than 1.05. Corresponding solutions of potassium aluminate can also be used.

The alkyltrialkoxysilanes suitable for the preparation of the solutions of the invention correspond to the formula $$R-Si(OR')_3$$

in which R is an aliphatic moiety of 1 to 8 carbon atoms and R is an aliphatic moiety of 1 to 4 carbon atoms.

In a special embodiment of the invention, a mixture of alkyltrialkoxysilanes is present in the aqueous solution.

The stability of the solutions in accordance with the invention is determined by the quantitative ratios of the silanes to the aluminate and to the solvent water. The amounts of silane are conveniently expressed hereinbelow as $SiO_2$ and those of aluminate as $Al_2O_3$.

The solutions of this invention are particularly stable when the molar ratio of the solvent water to the dissolved alkyltrialkoxysilane, expressed as $SiO_2$, is greater than 22:1, and the molar ratio of $SiO_2:Al_2O_3$ is equal to or less than 17:1. The preferred range is a molar ratio of water:$SiO_2$ of 22 to 45 and a molar ratio of $SiO_2:Al_2O_3$ equal to or less than 15. At high silane concentrations, the stability of such solutions ranges from several days to several months.

In a preferred embodiment of the invention, a methyltrialkoxysilane is used as the alkyltrialkoxysilane.

The solutions according to the invention are useful for the same purposes as the silanes themselves contained therein.

The following examples illustrate the present invention and will enable others skilled in the art to understand it more completely. It should be understood, however, that the invention is not limited solely to the particular examples given below.

In the following Examples 1 to 7 the aqueous solutions of the alkyltrialkoxysilane were prepared by acid-catalyzed hydrolysis (pH=3). The alkali metal aluminate, brought into aqueous solution by an excess of alkali metal hydroxide, was added to this solution. The amounts used and the stabilities are given in Table 1.

TABLE 1

| Example | Methyltrimethoxysilane [g] | Water [g] | $Al_2O_3$ [g] | $Na_2O$ [g] | Stability |
|---|---|---|---|---|---|
| 1 (for comparison) | 25 | 100 | — | — | 2 h 55 min |
| 2 (for comparison) | 25 | 200 | — | — | 5 h 10 min |
| 3 | 25 | 75.20 | 1.90 | 1.53 | 10 days |
| 4 | 25 | 100 | 1.90 | 1.53 | more than 6 months |
| 5 | 25 | 125 | 1.27 | 1.02 | more than 6 months |
| 6 | 25 | 100 | 1.88 | 1.52 | more than 1 month |
| 7 (for comparison) | 25 | 100 | 0.94 | 1.33 | 1 hour |

EXAMPLE 8

A mixture of 8 g of propyltrimethoxysilane and 32 g of methyltrimethoxysilane was dissolved in 160 g of water at pH 3. 11 ml of an aqueous sodium aluminate solution containing 22.9 wt.−% $Al_2O_3$ and 18 wt.−% $Na_2O$ (solution density 1.50 g/cm$^3$) were added. The stability of the solution was about 3 days.

EXAMPLE 8A (for comparison)

For the same mixture as in Example 8, but without the addition of the aluminate solution, the stability was only about 1 hour and 30 minutes.

EXAMPLE 9

A mixture of 4 g of propyltrimethoxysilane and 36 g of methyltrimethoxysilane was dissolved in 160 g of water at pH 3. 11 ml of an aqueous sodium aluminate solution containing 22.9 wt.−% $Al_2O_3$ and 18 wt.−% $Na_2O$ (solution density 1.50 g/cm$^3$) were added. The stability of the solution was more than 1 month.

EXAMPLE 9A (for comparison)

For the same mixture as in Example 9, but without the addition of the aluminate solution, the stability was only about 2 hours and 30 minutes.

EXAMPLE 10

20 g of methyltrimethoxysilane were dissolved in 100 g of water at pH 3. 5 ml of an aqueous potassium aluminate solution containing 22.25 wt.−% $Al_2O_3$ and 28.34 wt.−% $K_2O$ (solution density 1.57 g/cm$^3$) were added. The stability of the solution was more than 3 months.

EXAMPLE 11

A solution prepared as in Example 4 was refluxed at the boiling point for 4 hours. The solution easily clouded up, but was stable without precipitation for more than 3 months.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An aqueous solution of at least one alkyltrialkoxysilane of the formula $$R-Si(OR')_3$$

wherein R is an aliphatic moiety of 1 to 8 carbon atoms and R' is an aliphatic moiety of 1 to 4 carbon atoms, said solution comprising an alkali metal aluminate and an alkali metal hydroxide as stabilizers.

2. An aqueous solution of claim 1 comprising a mixture of 2 or more of said alkyltrialkoxysilanes.

3. An aqueous solution of claim 1, wherein the molar ratio of the solvent water to the dissolved alkyltrialkoxysilane, expressed as $SiO_2$, is greater than 22:1.

4. An aqueous solution of claim 1, wherein the molar ratio of dissolved alkyltrialkoxysilane, expressed as $SiO_2$, to the amount of alkali metal aluminate in the solution, expressed as $Al_2O_3$, is equal to or less than 17:1.

5. An aqueous solution of claim 1, wherein said alkyltrialkoxysilane is predominantly a methyltrialkoxysilane.

* * * * *